(12) United States Patent
Gutierrez et al.

(10) Patent No.: US 10,449,148 B2
(45) Date of Patent: Oct. 22, 2019

(54) DIETARY SUPPLEMENT FOR IMPROVING BRAIN HEALTH

(71) Applicant: BRAINGEAR ENTERPRISES, INC., San Francisco, CA (US)

(72) Inventors: Patricia Gutierrez, San Francisco, CA (US); Christina Beer, Salt Lake City, UT (US)

(73) Assignee: BRAINGEAR ENTERPRISES, INC., San Francisco, CA (US)

( * ) Notice: Subject to any disclaimer, the term of this patent is extended or adjusted under 35 U.S.C. 154(b) by 293 days.

(21) Appl. No.: 15/287,346

(22) Filed: Oct. 6, 2016

(65) Prior Publication Data

US 2017/0020815 A1 Jan. 26, 2017
US 2017/0360701 A2 Dec. 21, 2017
US 2018/0085310 A2 Mar. 29, 2018

Related U.S. Application Data

(60) Provisional application No. 62/250,854, filed on Nov. 4, 2015, provisional application No. 62/259,260, filed on Nov. 24, 2015.

(51) Int. Cl.

| | |
|---|---|
| *A61K 9/00* | (2006.01) |
| *A61K 31/593* | (2006.01) |
| *A61K 31/455* | (2006.01) |
| *A61K 31/4415* | (2006.01) |
| *A61K 31/714* | (2006.01) |
| *A61K 31/14* | (2006.01) |
| *A61K 31/198* | (2006.01) |
| *A61K 36/82* | (2006.01) |
| *A61K 31/4745* | (2006.01) |
| *A23L 2/52* | (2006.01) |
| *A61K 31/047* | (2006.01) |
| *A61K 31/194* | (2006.01) |
| *A61K 31/355* | (2006.01) |
| *A61K 31/4406* | (2006.01) |
| *A61K 31/59* | (2006.01) |
| *A61K 31/133* | (2006.01) |
| *A61K 31/225* | (2006.01) |

(52) U.S. Cl.
CPC .............. *A61K 9/0095* (2013.01); *A23L 2/52* (2013.01); *A61K 31/047* (2013.01); *A61K 31/133* (2013.01); *A61K 31/14* (2013.01); *A61K 31/194* (2013.01); *A61K 31/198* (2013.01); *A61K 31/225* (2013.01); *A61K 31/355* (2013.01); *A61K 31/4406* (2013.01); *A61K 31/4415* (2013.01); *A61K 31/455* (2013.01); *A61K 31/4745* (2013.01); *A61K 31/59* (2013.01); *A61K 31/593* (2013.01); *A61K 31/714* (2013.01); *A61K 36/82* (2013.01); *A23V 2002/00* (2013.01)

(58) Field of Classification Search
None
See application file for complete search history.

(56) References Cited

U.S. PATENT DOCUMENTS

| 7,976,879 B2 * | 7/2011 | Roizen | A23G 1/30 |
| | | | 424/451 |
| 8,088,431 B2 * | 1/2012 | Ward | A23G 1/32 |
| | | | 426/631 |
| 8,496,979 B1 * | 7/2013 | Hastings | A23L 33/15 |
| | | | 424/733 |

OTHER PUBLICATIONS

Alban, D., How Inositol Benefits These 6 Mental Health Conditions, http://bebrainfit.com/inositol-benefits-mental-health/, Accessed Jan. 3, 2018.
Alkadhi, K., Endplate channel actions of a hemicholinium-3 analog, DMAE, Naunyn-Schmiedeberg's Archives of Pharmacology, vol. 332, pp. 230-235, 1986.
Alves et al., Acetyl-l-Carnitine provides effective in vivo neuroprotection over 3,4-methylenedioximehtamphetamine-induced mitochondrial neurotoxicity in the adolescent rat brain, Neuroscience, vol. 158, pp. 514-523, 2009.
Alzforum, Trial Suggests Vitamin E Protects Function in Mild Alzheimer's, http://www.alzforum.org/news/research-news/trial-suggests-vitamin-e-protects-function-mild-alzheimers, Jan. 7, 2014, Accessed Dec. 14, 2017.
alzheimers.net, Benefits of Green Tea for Alzheimer's, https://www.alzheimers.net/2014-07-28/benefits-of-drinking-green-tea/, Jul. 28, 2014, Accessed Dec. 13, 2017.
Anderson, P., Vitamin D and Dementia: A very close tie, www.medscape.com/viewarticle/829508_print, Dated Aug. 6, 2014, Accessed Jan. 2, 2018.
Annweiler et al., 25-Hydroxyvitamin D, dementia, and cerebrovascular pathology in elders receiving home services, Neurology, vol. 75, pp. 95-96, 2010.
Atif et al., Progesterone with vitamin D affords better neuroprotection against excitotoxicity in cultured cortical neurons than progesterone alone, Molecular Medicine, vol. 15, pp. 328-336, 2009.
Bianchetti et al., Effects of acetyl-l-carnitine in alzheimer's disease patients unresponsive to acetylcholinesterase inhibitors, Current Medical Research and Opinion, vol. 19, 2003.
Blissreturned Word Press, Inositol : The vitamin that promotes healthy brain development and function, and works closely with choline to move fats out of the heart and liver, https://blissreturned.wordpress.com/2012/02/13/inositol-the-vitamin-that-promotes-healthy-brain-development-and-function-and-works-closely-with-choline-to-move-fats-out-of-the-heart-and-liver/, Feb. 13, 2012, Accessed Dec. 14, 2017.

(Continued)

*Primary Examiner* — Susan Hoffman
(74) *Attorney, Agent, or Firm* — Knobbe, Martens, Olson & Bear LLP

(57) ABSTRACT

Compositions that can be used to improve human health, and in particular brain health are provided. In some embodiments the composition comprises Inositol, N-Acetyl L-Tyrosine, pyrroloquinoline quinone (PQQ), Choline bitartrate, L-Theanine and Acetyl-L-Carnitine. The compositions may be administered to a subject, for example in the form of a liquid drink, to improve brain health.

17 Claims, No Drawings

(56) References Cited

OTHER PUBLICATIONS

Block, W., Acetyl L-Carnitine Protects Memory and Intellectual Functions Together with its ally lipoic acid, it retards aging by enhancing mitochondrial function, http://www.life-enhancement.com/magazine/article/1105-acetyl-l-carnitine-protects-memory-and-intellectual-functions, Aug. 2005, Accessed Dec. 14, 2017.
Block, W., Help Delay and Prevent Alzheimer's by whittling away amyloid-β neurotoxins that cause memory deficits, http://www.life-enhancement.com/magazine/article/2472-help-delay-and-prevent-alzheimers, Sep. 2011, Accessed Dec. 14, 2017.
Brauser, D., Citicoline may improve memory, decrease cognitive decline, Medscape Med News, www.medscape.com/viewarticle/780283_print, 2003.
Bryan et al., Short-term folate, vitamin b-12 or vitamin b-6 supplementation slightly affects memory performance but not mood in women of various ages, Journal of Nutrition, vol. 132, pp. 1345-1356, 2002.
Buckley, D., Is PQQ (Pyrroloquinoline Quinone) The ultimate anti-aging "vitamin" for your brain?, Natural Stacks Website, www.naturalstacks.com/blogs/news/pqq-brain-health, Oct. 25, 2017.
Buell et al., Vitamin D and neurocognitive dysfunction: preventing Decline?, Molecular Aspects of Medicine, vol. 29, No. 6, pp. 415-422, Dec. 2008.
Buell et al., Vitamin D is associated with cognitive function in elders receiving home health services, The Journals of Gerontology: Series A, vol. 64, No. 8, pp. 888-895, Aug. 2009.
Caruana et al., Polyphenolic compounds are novel protective agents against lipid membrane damage by a-synuclein aggregates in vitro, Biochimica et Biophysica Acta, vol. 1818, pp. 2502-2510, 2012.
Chengappa et al., Inositol as an add-on treatment for bipolar depression, Bipolar Disorders, vol. 2, pp. 47-55, 2000.
Chong et al., Nicotinamide modulates mitochondrial membrane potential and cysteine protease activity during cerebral vascular endothelial cell injury, Journal of Vascular Research, vol. 39, pp. 131-147, 2002.
Chowanadisai et al., Pyrroloquinoline quinone stimulates mitochondrial biogenesis through cAMP response element-binding protein phosphorylation and increased PGC-1aphph expression, Journal of Biological Chemistry, vol. 285, pp. 142-152, 2010.
Coppede F., One-carbon metabolism and alzheimer's disease: Focus on epigenetics, Current Genomics, vol. 11, pp. 246-260, 2010.
Daniells S., Vitamin E: The 'overlooked' nutrient and its brain health benefits, Nutra Ingredients, https://www.nutraingredients.com/Article/2013/10/22/Vitamin-E-The-overlooked-nutrient-and-its-brain-health-benefits, Oct. 21, 2013.
Dean et al., How to Improve Your Memory and Increase Your Intelligence Using the Latest Discoveries in Neuroscience, http://www.smart-publications.com/books/full-text/smart-drugs-and-nutrients/smart-drugs-and-nutrients-sec-5/smart-drugs-and-nutrients-sec5-dmae/, Published Jan. 1, 1991, Accessed Dec. 14, 2017.
Deijen et al., Tyrosine improves cognitive performance and reduces blood pressure in cadets after one week of a combat training course, Brain Research Bulletin, vol. 48, No. 2, pp. 203-209, 1999.
Douaud et al., Preventing Alzheimer's disease-related gray matter atrophy by B-vitamin treatment, PNAS, vol. 110, No. 23, pp. 9523-9528, Jun. 4, 2016.
Downey, M., Powerful Protection Against Cellular Aging, http://www.lifeextension.com/Magazine/2012/10/Powerful-Protection-Against-Cellular-Aging/Page-01?p=1, Oct. 2012, Accessed Dec. 13, 2017.
Egashira et al., Theanine prevents memory impairment induced by repeated cerebral ischemia in rats, Phytotherapy Research, vol. 22, pp. 65-68, 2008.
Eggersdorfer M., Boosting brain health: could vitamin E be the key to healthy aging?, DSM, https://www.dsm.com/campaigns/talkingnutrition/en_US/talkingnutrition-dsm-com/2017/11/Boosting-brain-health-could-vitamin-E-be-the-key-to-healthy-aging.html, Nov. 27, 2017.

Erdman et al., Nutrition and Traumatic Brain Injury: Improving acute and subacute health outcomes in military personnel, Institute of Medicine, National Academies Press, 2011.
ETH Zurich, Niacin, the fountain of youth, https://www.sciencedaily.com/releases/2013/09/130930101836.htm, Sep. 30, 2013, Accessed Dec. 14, 2017.
Evins et al., Inisitol augmentation of lithium or valproate for bipolar depression, Bipolar disorders, vol. 8, pp. 168-174, 2006.
Fernstrom, Tyrpsine, Phenylalanine, and catecholamine synthesis and function in the brain, Journal of Nutrition, vol. 137, pp. 1539-1547, 2007.
Finkel, J., Dr. L. Ray Matthews Unleashes the Power of Vitamin D, http://www.lifeextension.com/magazine/2013/10/Dr-L-Ray-Matthews-Unleashes-the-Power-of-Vitamin-D/Page-01, Oct. 2013, Accessed Dec. 14, 2017.
Flagg, M., Reverse Brain Cell Death by Growing New Mitochondria, http://www.lifeextension.com/Magazine/2011/11/Reverse-Brain-Cell-Death-by-Growing-New-Mitochondria/Page-01, Nov. 2011, Accessed Dec. 13, 2017.
George, S., Brain Food and Egg Yolks, https://www.livestrong.com/article/547888-brain-food-and-egg-yolks/, Oct. 3, 2017, Accessed Dec. 14, 2017.
Gestuvo et al., Common Dietary Supplements for Cognitive Health, Aging Health, vol. 8, No. 1, pp. 89-87, 2012.
Graff-Radford, J., Vitamin B-12: Can it improve memory in Alzheimer's?—Can vitamin B-12 improve memory in Alzheimer's disease?, https://www.mayoclinic.org/diseases-conditions/alzheimers-disease/expert-answers/alzheimers/faq-20057895, Oct. 14, 2016, Accessed Dec. 14, 2017.
Gray, N., Choline may help protect the brain from effects of ageing, https://www.nutraingredients.com/Article/2011/11/30/Choline-may-help-protect-the-brain-from-effects-of-ageing, Nov. 30, 2011, Accessed Dec. 14, 2017.
Green et al., Nicotinamide restores cognition in Alzheimer's disease transgenic mice via a mechanism involving sirtuin inhibition and selective reduction of Thr231-phosphotau, Journal of Neuroscience, vol. 28, No. 45, pp. 11,500-11,510, 2008.
Hageman et al., Niacin, poly(ADP-riboseti polymerase-1 and genomic stability, Mutation Research, vol. 475, pp. 45-56, 2001.
Hall-Flavin, D., Vitamin B-12 and depression: Are they related?—What's the relationship between vitamin B-12 and depression?, https://www.mayoclinic.org/diseases-conditions/depression/expert-answers/vitamin-b12-and-depression/faq-20058077, Nov. 23, 2016, Accessed Dec. 14, 2017.
Harris et al., Dietary pyrroloquinoline quinone (PQQ) alters indicators of inflammation and mitochondrial-related metabolism in human subjects, Journal of Nutritional Biochemistry, vol. 24, No. 12, pp. 2076-2084, Dec. 2013.
Harvard T.H. Chan School of Public Health, Vitamin E and Health, https://www.hsph.harvard.edu/nutritionsource/vitamin-e/, Accessed Dec. 14, 2017.
Health Supplements Nutritional Guide, Inositol, http://www.healthsupplementsnutritionalguide.com/inositol/, Accessed Dec. 14, 2017.
Heerema, E., Is It Alzheimer's Disease or Vitamin B12 Deficiency?, https://www.verywell.com/is-it-alzheimers-disease-or-vitamin-b12-deficiency-98738, Jul. 28, 2017, Accessed Dec. 14, 2017.
helpguide.org, What's Causing Your Memory Loss?—It's Not Necessarily Alzheimer's, https://www.helpguide.org/harvard/whats-causing-your-memory-loss.htm, Accessed Dec. 14, 2017.
Helsingin Yliopisto (University of Helsinki), Energizing sick mitochondria with vitamin B3: Effective treatment for mitochondrial disease, https://www.sciencedaily.com/releases/2014/04/140407090403.htm, Apr. 7, 2014, Accessed Dec. 14, 2017.
Himmelheber, et al., Increases in cortical acetylcholine release during sustained attention performance in rats, Cognitive Brain Research, vol. 9, pp. 313-325, 2000.
Hitti, M., Green Tea May Do Wonders for the Brain, https://www.webmd.com/food-recipes/news/20060217/green-tea-may-do-wonders-for-brain#1, Feb. 17, 2006, Accessed Dec. 13, 2017.
Hoffman et al., The effects of acute and prolonged CRAM supplementation on reaction time and subjective measures of focus and

(56) References Cited

OTHER PUBLICATIONS alertness in healthy college students, Journal of the International Society of Sports Nutrition, vol. 7, pp. 39, Dec. 15, 2010.
Hopkins, C., How PQQ protects the brain, Life Extension Magazine, http://www.lifeextension.com/Magazine/2016/4/How-PQQ-Protects-the-Brain/Page-01, Apr. 2016.
Hudson et al., Acetyl-l-carnitine for dementia, Cochrane database of Systematic reviews, vol. 2003, Iss. 2, 2008.
Jenkins, J., Information on Supplements That Help Neurotransmitters in Brain, https://www.livestrong.com/article/169609-information-on-supplements-that-help-neurotransmitters-in-brain/, Oct. 3, 2017, Accessed Dec. 14, 2017.
Jennings KA., 9 Science-based benefits of niacin (vitamin B3), Healthline, https://www.healthline.com/nutrition/niacin-benefits#section2, Dec. 2, 2016.
Jensen, A., Vitamin E Keeps Your Brain Razor-Sharp—For those with suboptimal levels, it can improve cognitive age by 8-9 years, http://www.life-enhancement.com/magazine/article/730-vitamin-e-keeps-your-brain-razor-sharp, Nov. 2002, Accessed Dec. 14, 2017.
Jones et al., Acylcarnitines: Role in brain, Progress in lipid research, vol. 49, pp. 61-75, 2010.
Kakuda T, Neuroprotective effects of the green tea components theanine and catechins, Biological and pharmaceutical bulletin, vol. 25, No. 12, pp, 1513-1518, Dec. 2002.
Kalita et al., Vitamin B12 deficiency neurological syndromes: correlation of clinical, MRI and cognitive evoked potential, Journal of Neurology, vol. 255, pp. 353-359, Mar. 20, 2008.
Kang et al., A randomized trial of vitamin E supplementation and cognitive function in women, Archive of Internal Medicine, vol. 166, No. 22, pp. 2462-2468, 2006.
Keller D., Green tea linked to lower risk for cognitive decline, Medscape Medical News, www.medscape.com/viewarticle/842042_print, Mar. 25, 2015.
Kelly et al., L-theanine and caffeine in combination affect human cognition as evidenced by oscillatory alpha-band activity and attention task performance, Journal of Nutrition, vol. 138, pp. 1572-1577, 2008.
Kennedy, D., B Vitamins and the Brain: Mechanisms, dose and efficacy—A review, Nutrients, vol. 8, 2016.
Khan et al., Effective treatment of mitochondrial myopathy by nicotinamide riboside, a vitamin B3, EMBO Molecular Medicine, DOI: 10.1002/emmm.2O14O3943, Apr. 2014.
Kim et al., Association between intake of B vitamins and cognitive function in elderly Koreans with cognitive impairment, Nutrition Journal, vol. 13, 2014.
King, J., The Effects of N-Acetyl L-Tyrosine, https://www.livestrong.com/article/494776-the-effects-of-n-acetyl-l-tyrosine/, Oct. 3, 2017, Accessed Dec. 13, 2017.
Lifer, S., All About Supplements: DMAE The smart supplement, Life Extention Magazine, http://www.lifeextension.com/Magazine/2004/11/aas/Page-01, Nov. 2004.
Lake, J., Acetyl-l-carnitine: Important for Mental health, Psychology Today Website, https://www.psychologytoday.com/blog/integrative-mental-health-care/201710/acetyl-l-carnitine-important-mental-health, Oct. 6, 2017.
Levin et al., Effects of nicotinic dimethylaminoethyl esters on working memory performance of rats in the radial-arm maze, Pharmacology Biochemistry and Behavior, vol. 51, No's. 2-3, pp. 369-373, 1995.
Levine, J., Controlled trials of inositol in psychiatry, European Neuropsychopharmacology, vol. 7, pp. 147-155, 1997.
Life Enhancement, DMAE, http://www.life-enhancement.com/magazine/article/105-presence-of-mind-dmae-the-mood-elevating-smart-nutrient, Sep. 1997, Accessed Dec. 14, 2017.
Liftmode.com, Top 6 l-theanine benefits: What people are using this supplement for!, http://liftmode.com/blog/l-theanine-benefits/, Feb. 27, 2017.
Linnaeus, T., The Effects of Acetyl-L-Carnitine on Brain Waves, https://www.livestrong.com/article/468428-the-effects-of-acetyl-l-carnitine-on-brain-waves/, Oct. 3, 2017, Accessed Dec. 14, 2017.

Magill et al., Effects of tyrosine, phentermine, caffeine d-amphetamine, and placebo on cognitive and motor performance deficits during sleep deprivation, Nutritional Neuroscience, vol. 6, No. 4, pp. 237-246, Aug. 2003.
Malouf et al., Vitamin B6 for cognition(review), The Cochrane Database of Systematic Reviews 2003, Issue 4. 2008.
Mandel et al., Targeting multiple neurodegenerative diseases etiologies with multimodal-acting green tea catechins, The Journal of Nutrition, vol. 138, pp. 1578S-1583S, 2008.
Marcone, P., Generate Fresh Mitochondria with PQQ, http://www.lifeextension.com/magazine/2011/2/generate-fresh-mitochondria-with-pqq/page-01, Feb. 2011, Accessed Dec. 13, 2017.
Maxwell et al., Supplemental use of antioxidant vitamins and subsequent risk of cognitive decline and dementia, Dementia Geriatric Cognitive Disorders, vol. 20, No. 1, pp. 45-51, 2005.
Melville, N., 'Alarming' Vitamin D deficiencies in NFL football players, Medscape Medical News, https://www.medscape.com/viewarticle/746310_print, Jul. 13, 2011.
Mercola, Studies Show Cinnamon and B Vitamins can Help Prevent Alzheimer's, http://healthimpactnews.com/2013/studies-show-cinnamon-and-b-vitamins-can-help-prevent-alzheimers/, Jun. 14, 2013, Accessed Dec. 13, 2017.
Mercola, Vitamin B May Protect Against Alzheimer's, Say Researchers, https://articles.mercola.com/sites/articles/archive/2013/06/03/vitamin-b.aspx, Jun. 3, 2013, Accessed Dec. 13, 2017.
Meschino, J., Choline Supplementation for the Aging Brain and Other Therapeutic Applications, Dynamic Chiropractic, vol. 23, No. 24, http://www.dynamicchiropractic.com/mpacms/dc/article.php?id=50496, Nov. 20, 2005, Accessed Jan. 15, 2018.
Miller, A., Vitamin B-12 & Serotonin, https://www.livestrong.com/article/486425-vitamin-b-12-serotonin/; Oct. 3, 2017; Accessed Dec. 14, 2017.
Miller, J., Assessing the association between vitamin B-12 status and cognitive function in older adults, American Journal of Clinical Nutrition, vol. 84, pp. 1259-1260, 2006.
Milman et al., Vitamin E supplementation reduces cardiovascular events in a subgroup of middle-aged individuals with both type 2 diabetes mellitus and the haptoglobin 2-2 genotype: a prospective double-blinded clinical trial, Arteriosclerosis Thrombosis and Vascular Biology, vol. 28, pp. 341-347, 2008.
Mitchell, T., Broad-Spectrum Effects of Grape Seed Extract, http://www.lifeextension.com/magazine/2005/7/report_grapeseed/page-01, Jul. 2005, Accessed Dec. 14, 2017.
Moore, S., Benefits of Acetyl L Tyrosine, https://www.livestrong.com/article/264091-benefits-of-acetyl-l-tyrosine/, Oct. 3, 2017, Accessed Dec. 13, 2017.
Moorthy et al., Status of Vitamins B-12 and B-6 but not of folate, homocysteine, and the methylenetetrahydrofolate reduced C677T polymorphism are associated with impaired cognition and depression in adults, The Journal of Nutrition, vol. 142, pp. 1554-1560, 2012.
Nakashima et al., Influence of nicotinic acid on cerebroside synthesis in the brain of developing rats, Journal of Nutritional Science and Vitaminology, vol. 30, pp. 525-534, 1984.
Nalecz et al., Carnitine: Transport and physiological functions in the brain, Molecular aspects of medicine, vol. 25, pp. 551-567, 2004.
Nathan et al., The neuropharmacology of l-theanine(N-ethyl-l-glutamine): a possible neuroprotective and cognitive enhancing agent, Journal of Herbal Pharmacotherapy, vol. 6, pp. 21-30, 2006.
Neuhauser et al., Utilization of N-acetyl-l-tyrosine and glycyl-l-tyrosine during long-term parenteral nutrition in the growing rat, American Journal of Clinical Nutrition, vol. 42, pp. 585-596, 1985.
Neuroscience News Website, How green tea extract could help protect against alzheimer's, http://neurosciencenews.com/green-tea-extract-alzheimers-7724/, Oct. 11, 2017.
Nobre et al., L-theanine, a natural constituent in tea, and its effect on mental state, Asia Pacific Journal of Clinical Nutrition, vol. 17, pp. 167-168, 2008.
Nootriment, Can DMAE Supplements Make You Smarter and Keep you Young?, https://nootriment.com/dmae-supplements/, Accessed Dec. 14, 2017.
Nootriment, Inositol Effects on your Brain & Body, https://nootriment.com/inositol-effects/, Accessed Dec. 14, 2017.

(56) References Cited

OTHER PUBLICATIONS

Nootriment, L-Tyrosine Effects on Stress, Mood and your Brain, https://nootriment.com/l-tyrosine-effects/, Accessed Dec. 13, 2017.

Ohwada et al., Pyrroloquinoline quinone (PQQ) prevents cognitive deficit caused by oxidative stress in rats, Journal of Clinical Biochemistry and Nutrition, vol. 42, pp. 29-34, Jan. 2008.

Olthof et al., Choline supplemented as phosphatidylcholine decreases fasting and postmethionine-loading plasma homocysteine concentrations in healthy men, American Journal of Clinical Nutrition, vol. 82, No. 1, pp. 111-117, (PubMed), 2005.

Oregon State University, Mechanism outlined by which inadequate vitamin E can cause brain damage, http://oregonstate.edu/ua/ncs/archives/2015/apr/mechanism-outlined-which-inadequate-vitamin-e-can-cause-brain-damage, Apr. 13, 2015, Accessed Dec. 14, 2017.

Oregon State University, Vitamin B6, http://lpi.oregonstate.edu/mic/vitamins/vitamin-B6, Originally Written—2000; Updated—2002, 2007, and 2014, Accessed Dec. 13, 2017.

Orthomolecular Medicine News Service, High Doses of Vitamins Fight Alzheimer's Disease—Why Don't Doctors Recommend Them Now?, http://orthomolecular.org/resources/omns/v04n25.shtml, Dec. 9, 2008, Accessed Dec. 14, 2017.

Pacelli et al., Dietary choline deprivation impairs rat brain mitochondrial function and behavioral phenotype, The Journal of Nutrition, vol. 140, pp. 1072-1079, 2010.

Pearson et al., Choline in Brain Function and Sleep, http://www.life-enhancement.com/magazine/article/2863-choline-in-brain-function-and-sleep, May 2013, Accessed Dec. 14, 2017.

Petersen et al., Vitamin E and donepezil for the treatment of mild cognitive impairment, New England Journal of Medicine, vol. 352, No. 23, pp. 2379-2388, 2005.

Pettegrew et al., Clinical and neurochemical effects of acetyl-L-carnitine in Alzheimer's disease, Neurobiology of Aging, vol. 16, No. 1, pp. 1-4, 1995.

Pitt et al., Protection against the synaptic targeting and toxicity of Alzheimer's-associated Aβ oligomers by insulin mimetic chiro-inositols, The FASEB Journal, vol. 27, No. 1, pp. 199-207, doi: 10.1096/fj.12-211896, Epub Oct. 16, 2012, Jan. 2013.

Poly et al., The relation of dietary choline to cognitive performance and white-majer hyperintensity in the Framingham Offspring Cohort, American Journal of Clinical Nutrition, vol. 94, No. 6, pp. 1584-1591, doi: 10.3945/ajcn.110.008938, Epub Nov. 9, 2011, Dec. 2011.

Rawling et al., Dietary niacin deficiency lowers tissue poly(ADP-ribose) and NAD+ concentrations in Fischer-344 rats, Journal of Nutrition, vol. 124, pp, 1597-1603, 1994.

Renee, J., What Is a DMAE Supplement?, https://www.livestrong.com/article/263359-what-is-a-dmae-supplement/, Oct. 3, 2017, Accessed Dec. 14, 2017.

Rezai-Zadeh et al., Green tea epigallocatechin-3-gallate (EGCG) reduces beta-amyloid mediated cognitive impairment and modulates tau pathology in Alzheimer transgenic mice, Brain Research, vol. 1214, pp. 177-187, 2008.

Richards, B., Acetyl-l-Carnitine—Anti-Aging for Brain Cells & Metabolism, https://www.wellnessresources.com/news/acetyl-l-carnitine-anti-aging-for-brain-cells-and-metabolism, Dec. 17, 2012, Accessed Dec. 14, 2017.

Richards, B., Green Tea May Reduce Amyloid Brain Tangles of Cognitive Dec, https://www.wellnessresources.com/news/green-tea-may-reduce-amyloid-brain-tangles-of-cognitive-decline, Mar. 13, 2013, Accessed Dec. 13, 2017.

Richards, B., How to Recover from a Concussion—Athletes Take Note, https://www.wellnessresources.com/news/how-to-recover-from-a-concussion-athletes-take-note, Jul. 29, 2011, Accessed Dec. 14, 2017.

Richards, B., Tyrosine Helps Maintain Mental Ability Under Stress, https://www.wellnessresources.com/news/tyrosine-helps-maintain-mental-ability-under-stress, Feb. 14, 2014, Accessed Dec. 13, 2017.

Richards, K., Rejuvenating the Brain—How PQQ Helps Power Up Mental Processing, http://www.prohealth.com/library/showarticle.cfm?libid=16896, Mar. 30, 2012, Accessed Dec. 13, 2017.

Riggs et al., Relations pf vitamin B-12, vitamin B-6, folate, and homocysteine to cognitive performance in the normative aging study, American Journal of Clinical Nutrition, vol. 63, pp. 306-314, 1996.

Roseland, J., L-Tyrosine (N-Acetyl-Tyrosine)—This amino acid is a harbinger of two of the most important neurotransmitters, dopamine and norepinephrine, http://www.limitlessmindset.com/nootropic-ingredients/323-l-tyrosine.html, Accessed Dec. 13, 2017.

Sanford A., Brain benefits of L-theanine, Life Extention Magazine, http://www.lifeextension.com/Magazine/2016/3/Brain-Benefits-of-L-Theanine/Page-01, Mar. 2016.

Schmidt et al., Green tea extract enhances parieto-frontal connectivity during working memory processing, Psychopharmacology, vol. 231, pp. 3879-3888, 2014.

ScienceDaily Website, Antioxidant therapy may have promising potential in concussion treatment, https://www.sciencedaily.com/releases/2015/04/150401132752.htm, Apr. 1, 2015.

Shaw et al., Choline and risk of neural tube defects in a folate-fortified population, Epidemiology, vol. 20, No. 5, pp. 714-719, 2009.

Society for Neuroscience, Grape Seed Extract May Reduce Cognitive Decline Associated With Alzheimer's Disease, https://www.sciencedaily.com/releases/2008/06/080617165716.htm, Jun. 18, 2008, Accessed Dec. 14, 2017.

Stites, et al. Pyrroloquinoline quinone modulates mitochondrial quantity and function in mice. Journal of Nutrition, vol. 136, pp. 390-396, 2006.

Summers, A., What are the Benefits of Inositol and Choline?, https://www.livestrong.com/article/259379-what-are-the-benefits-of-the-vitamins-inositol-choline/, Oct. 3, 2017, Accessed Dec. 14, 2017.

Taylor et al., Inositol for depressive disorders; Cochrane database of systemic reviews 2004, Issue 1, 2009.

The Mount Sinai Hospital / Mount Sinai School of Medicine, Natural chemical found in grapes may protect against Alzheimer's disease, https://www.sciencedaily.com/releases/2011/07/110715135211.htm, Jul. 18, 2011, Accessed Dec. 14, 2017.

Tomen D., Vitamin B3(Niacin), Nootropics Expert Website, http://nootropicsexpert.com/vitamin-b3-niacin/, Accessed Jan. 3, 2018.

Tomen D., Vitamin B6(Pyridoxine), Nootropics Expert Website, http://nootropicsexpert.com/vitamin-b6-pyridoxine/, Accessed Jan. 9, 2018.

University Health News, Protect Your Brain with Powerful PQQ Supplement Benefits, https://universityhealthnews.com/daily/memory/protect-your-brain-with-powerful-pqq-supplement-benefits/, Aug. 14, 2015, Accessed Dec. 13, 2017.

University of Basel, Green tea extract boosts your brain power, especially the working memory, new research shows, https://www.sciencedaily.com/releases/2014/04/140407101545.htm, Apr. 7, 2014, Accessed Dec. 13, 2017.

University of Granada, Vitamin B: Choline intake improves memory and attention-holding capacity, experts say, https://www.sciencedaily.com/releases/2013/07/130711103239.htm, Jul. 11, 2013, Accessed Dec. 14, 2017.

University of Kentucky, Commonly used supplement may improve recovery from spinal cord injuries, https://www.sciencedaily.com/releases/2011/09/110928185025.htm, Sep. 29, 2011, Accessed Dec. 14, 2017.

University of Kentucky, New study suggests low vitamin D causes damage to brain, https://www.sciencedaily.com/releases/2013/12/131202121101.htm, Dec. 2, 2013, Accessed Dec. 14, 2017.

University of Maryland Medical Center, Tyrosine, http://www.umm.edu/health/medical/altmed/supplement/tyrosine, Jul. 16, 2013, Accessed Dec. 13, 2017.

University of Maryland Medical Center, Vitamin B6 (Pyridoxine), http://www.umm.edu/health/medical/altmed/supplement/vitamin-b6-pyridoxine, Aug. 5, 2015, Accessed Dec. 13, 2017.

University of Oxford, B vitamins slow brain atrophy in people with memory problems, https://www.sciencedaily.com/releases/2010/09/100912213050.htm, Sep. 14, 2010, Accessed Dec. 13, 2017.

(56) References Cited

OTHER PUBLICATIONS

UT Southwestern Medical Center, Researchers evaluate red wine compound for treating concussions in pro boxers, https://www.sciencedaily.com/releases/2011/05/110526064800,htm, May 27, 2011, Accessed Dec. 14, 2017.

Virmani et al., Role of carnitine esters in brain neuropathology, Molecular Aspects of Medicine, vol. 25, No. 5-6, pp. 533-549, 2004.

Walton, A., Green Tea Compound may protect body and brain, Forbes Website, https://www.forbes.com/sites/alicegwalton/2017/07/31/green-tea-compound-may-protect-body-and-brain/#7a764b391c3b, Jul. 31, 2017.

WebMD, Deanol, https://www.webmd.com/vitamins-supplements/ingredientmono-524-deanol.aspx?activeingredientid=524&activeingredientname=deanol, Accessed Dec. 14, 2017.

Wei et al., Folate/vitamin-B12 prevents chronic hyperhomocysteinemia-induced tau hyperphosphorylation and memory deficits in aged rats, Journal of Alzheimers Disease, vol. 27, No. 3, pp. 639-650, 2011.

Wentz, L., Vitamin D Status May Affect Resilience and Recovery from Mild Traumatic Brain Injury in Military Personnel, http://austinpublishinggroup.com/nutrition-food-sciences/fulltext/ajnfs-v2-id1030.php, May 9, 2014, Accessed Dec. 14, 2017.

Williams et al., Bioactivity profiling with parallel mass spectrometry reveals an assemblage of green tea metabolites affording protection against human huntingtin and a-synuclein toxicity, Journal of Agriculture and Food Chemistry, vol. 55, No. 23, pp. 9450-9456, 2007.

Wurtman et al., Precursor control of neurotransmitter synthesis, Pharmacological Reviews, vol. 32, No. 4, pp. 315-335, 1981.

Xie et al., Promotion of neuronal plasticity by (−)-epigallocatechin-3-gallate, Neurochemical Research, vol. 33, pp. 776-783, 2008.

Yamaguchi et al., Stimulation of nerve growth factor production by pyrroloquinoline quinone and its derivatives in vitro and in vivo, Bioscience, Biotechnology, and Bioscience, vol. 57, No. 7, pp. 1231-1233, 1993.

Yoto et al., Effects of L-theanine or caffeine intake on changes in blood pressure under physical and psychological stresses, Journal of Physiological Anthropology, vol. 31, 2012.

Zeisel, SH, Choline: an essential nutrient for humans, Nutrition, vol. 16, No. 7-8, pp. 669-671, 2000.

Zhang et al., Combined R-a—lipoic acid and acetyl-L-carnitine exerts efficient preventative effects in a cellular model of Parkinson's disease, Journal of Cellular and Molecular Medicine, vol. 14, No. 1-2, pp. 215-225, 2010.

\* cited by examiner

DIETARY SUPPLEMENT FOR IMPROVING BRAIN HEALTH

CROSS REFERENCE TO RELATED APPLICATIONS

This application claims the benefit of U.S. Provisional Application No. 62/250,854, filed on Nov. 4, 2015, and U.S. Provisional Application No. 62/259,260, filed on Nov. 24, 2015, each of which is hereby incorporated by reference in its entirety.

FIELD

The present disclosure relates to compositions and their use for improving human health, in particular, human brain health. The compositions are intended, in some aspects, to support brain health, especially six key areas of brain health: neurotransmission support, axon regeneration support, BACE1 metabolism/inhibition, tau-protein metabolism/inhibition, mitochondrial function, and antioxidant protection.

General health improvements observable after taking the composition may include improvements to vascular health, improvements to neuronal health and/or improvements to brain health. In some embodiments, the improvements to brain health may include, but are not limited to, high levels of concentration, optimal cognitive function, effective decision making, keen comprehension, effortless recall, mental clarity, quick reflexes, restful sleep, increased motivation, coordinated motor function, efficient problem solving, mental acuity, optimal energy levels, overall well-being, ability to focus, mood stability, memory support, alertness, improved neurotransmission, and nerve cell integrity.

The composition may also be seen to provide benefits to subjects suffering from Post Traumatic Stress Disorder (PTSD), Attention Deficit Disorder (ADD), Attention Deficit Hyperactivity Disorder (ADHD), anxiety, migraine, dementia, tinnitus and hangovers.

SUMMARY

In some embodiments, a liquid drink comprising Acetyl L-Carnitine, Choline, Inositol, N-Acetyl L-Tyrosine, L-Theanine and Pyrroloquinoline Quinone (PQQ) is provided. In some embodiments the liquid drink additionally comprises Dimethylaminoethyl (DMAE) bitartrate. In some embodiments, the liquid drink additionally comprises one or more of Vitamin E, Vitamin D, Niacin, Vitamin B6, Vitamin B12, and Green tea extract.

In some embodiments, the liquid drink additionally comprises one or more of alpha-GPC (alpha-glycerylphosphorylcholine), Citicholine, Phosphatidylserine, Astaxanthin, Flaxseed, MCT (Medium Chain Triglycerides), Whole Coffee Fruit extract, *Ginko biloba*, Vinpocetine, *Panax ginseng*, Ashwaghanda, *Bacopa monnieri*, Grape seed extract, dark skinned berries and fruits known for their high concentrations of polyphenols/anthocyanidins, omega-3 fatty acids, omega-6 fatty acids, omega-9 fatty acids, Huperzine A, alpha-Lipoic acid, Magnesium and Zinc.

In some embodiments the liquid drink may additionally comprise one or more natural flavors and/or natural sweeteners. For example, the liquid drink may comprise sweeteners such as sugar, fructose, honey, erythritol, xylitol, stevia, talin, monk fruit, agave, citrus and protein extracts or combinations thereof.

In some embodiments, the liquid drink comprises one or more of propylene glycol, xanthan gum, guar gum, acacia gum; fillers; rice flour, methylcellulose, and magnesium stearate. In some embodiments, the liquid drink additionally comprises one or more flavoring agents. In some embodiments, the liquid drink additionally comprises one or more artificial sweeteners or one or more natural sweeteners or a combination thereof. In some embodiments, the liquid drink additionally comprises one or more preservatives.

In some embodiments, methods of improving brain health in a human subject are provided. In some embodiments, the methods comprise administering to the human subject a composition comprising Acetyl L-Carnitine, Choline, Inositol, N-Acetyl L-Tyrosine, L-Theanine and pyrroloquinoline quinone (PQQ). In some embodiments the composition additionally comprises Dimethylaminoethyl (DMAE) bitartrate. In some embodiments of the methods, the composition is administered in the form of a liquid drink as described herein.

In some embodiments, the composition additionally comprises one or more of Vitamin E, Vitamin D, Niacin, Vitamin B6, Vitamin B12, and Green tea extract. The liquid drink may additionally comprise one or more of alpha-GPC (alpha-glycerylphosphorylcholine), Citicholine, Phosphatidylserine, Astaxanthin, Flaxseed, MCT (Medium Chain Triglycerides), Whole Coffee Fruit extract, *Ginko biloba*, Vinpocetine, *Panax ginseng*, Ashwaghanda, *Bacopa monnieri*, Grape seed extract, dark skinned berries and fruits known for their high concentrations of polyphenols/anthocyanidins, omega-3 fatty acids, omega-6 fatty acids, omega-9 fatty acids, Huperzine A, alpha-Lipoic acid, Magnesium and Zinc.

In some embodiments the composition may additionally comprise one or more natural flavors and/or natural sweeteners. For example, the liquid drink may comprise sweeteners such as sugar, fructose, honey, erythritol, xylitol, stevia, talin, monk fruit, agave, citrus and protein extracts or combinations thereof.

In some embodiments of the method, the composition additionally comprises one or more of propylene glycol, xanthan gum, guar gum, acacia gum; fillers; rice flour, methylcellulose, magnesium stearate. In some embodiments of the method, the composition additionally comprises one or more flavoring agents. In some embodiments of the method, the composition additionally comprises one or more artificial sweeteners or one or more natural sweeteners or a combination thereof. In some embodiments of the method, the composition additionally comprises one or more preservatives.

DETAILED DESCRIPTION

There is a need for a composition comprising ingredients that support brain health. The present disclosure relates to compositions which are dietary supplements that may be useful for supporting and improving human health, and in particular human brain health. Also described are methods for using the composition, such as for improving human health, particularly brain health. Also provided are kits, comprising the composition to be consumed according to a dietary regimen for improving brain health.

In some embodiments the composition comprises Acetyl L-Carnitine, Choline, Inositol, N-Acetyl L-Tyrosine, L-Theanine and pyrroloquinoline quinone (PQQ) as active ingredients. In some embodiments the composition additionally comprises Dimethylaminoethyl (DMAE) bitartrate.

In some embodiments the composition comprises Inositol, N-Acetyl L-Tyrosine, Dimethylaminoethyl (DMAE)

bitartrate, pyrroloquinoline quinone (PQQ), Acetyl-L-Carnitine, L-Theanine and Choline bitartrate as active ingredients.

In some embodiments the composition may comprise one or more of Vitamin E, Vitamin D, Niacin, Vitamin B6, Vitamin B12, and Green Tea extract.

In some embodiments the composition comprises Acetyl L-Carnitine, Inositol, N-Acetyl L-Tyrosine, L-Theanine and pyrroloquinoline quinone (PQQ), as well as one or more of Dimethylaminoethyl (DMAE) bitartrate, Vitamin E, Vitamin D, Niacin, Vitamin B6, Vitamin B12, and Green Tea extract as active ingredients.

In some embodiments the composition comprises Inositol, N-Acetyl L-Tyrosine, Dimethylaminoethyl (DMAE) bitartrate, L-Theanine, pyrroloquinoline quinone (PQQ), Acetyl-L-Carnitine, Choline bitartrate and one or more of Vitamin E, Vitamin D, Niacin, Vitamin B6, Vitamin B12, and Green Tea extract as active ingredients.

In some embodiments the composition comprises at least Inositol, N-Acetyl L-Tyrosine, Dimethylaminoethyl (DMAE) bitartrate, pyrroloquinoline quinone (PQQ), Acetyl-L-Carnitine, Choline bitartrate, L-Theanine, Vitamin E, Vitamin D, Niacin, Vitamin B6, Vitamin B12, and Green Tea extract as active ingredients.

In some embodiments the composition may comprise one or more additional active ingredients such as alpha-GPC (alpha-glycerylphosphorylcholine), Citicholine, Phosphatidylserine, Astaxanthin, Flaxseed, MCT (Medium Chain Triglycerides), Whole Coffee Fruit extract, *Ginko biloba*, Vinpocetine, *Panax ginseng*, Ashwaghanda, *Bacopa monnieri*, Grape seed extract, dark skinned berries and fruits known for their high concentrations of polyphenols/anthocyanidins, omega-3 fatty acids, omega-6 fatty acids, omega-9 fatty acids, Huperzine A, alpha-Lipoic acid, Magnesium and Zinc.

In some embodiments the composition is provided in the form of a liquid drink. The liquid drink may comprise the active ingredients in a water base, or in another base liquid that is inert with respect to the active ingredients. The liquid drink may comprise one or more additional inactive ingredients. In some embodiment the liquid drink may comprise one or more gelling or stabilizing agents including, but not limited, to xanthan gum, guar gum, propylene glycol, acacia gum and maltodextrin. In some embodiments the liquid drink may comprise one or more colorants, for example a natural color such as carmine or beet root. In some embodiments the liquid drink may comprise one or more preservatives such as citrus oil, sorbates and benzoates. The liquid drink may also comprise one or more flavors such as fruit (e.g. strawberry, melon, etc.) and non-fruit flavors. In some embodiments the flavor is a natural flavor. In some embodiments the liquid drink may comprise artificial and natural sweeteners.

In some embodiments the composition comprises, but not limited to, one or more artificial sweeteners such as sucralose, acesulfame K or a combination of these and/or one or more natural sweeteners such as sugar, fructose, honey, erythritol, xylitol, stevia, monk fruit, agave, citrus and protein extracts used as sweeteners or combinations thereof.

In some embodiments the composition is provided in the form of a tablet, capsule, gel cap, or softgel. The tablet, capsule, gel cap, or softgel may comprise additional inactive ingredients such as fillers including, but not limited to, rice flour, methylcellulose, magnesium stearate. Several tablets, capsules, gel caps, or softgels typically comprise one daily dose of each of the active ingredients, as described below.

The combination of active ingredients provides health benefits when administered to a human subject, particularly brain health benefits. For example, in some embodiments the composition targets six key factors that are important to brain health. These include neurotransmission, axon regeneration, BACE1 metabolism/inhibition, tau-protein metabolism/inhibition, mitochondrial function, and antioxidant protection.

The active ingredients of the composition provide support for the various aspects of brain health. For example, in some embodiments neurotransmission may be supported by PQQ, DMAE bitartrate, Vitamin D, Choline, Inositol, Vitamin B12, Vitamin B6, Acetyl-L-Carnitine, N-Acetyl L-Tyrosine, L-Theanine, and Green Tea extract. In some embodiments, antioxidant protection may be provided by PQQ, Green Tea extract, Acetyl-L-Carnitine, L-Theanine, N-acetyl L-Tyrosine; Axon regeneration support by PQQ, Niacin, Vitamin D, Green Tea extract. In some embodiments, mitochondrial function may be supported by PQQ, Niacin, Vitamin D, Choline, Inositol, L-Theanine and Acetyl-L-Carnitine. In some embodiments tau protein metabolism may be supported by Vitamin B6, Vitamin B12, and BACE1 metabolism by DMAE bitartrate, Choline, Inositol, and Vitamin B6.

Thus, in some embodiments the composition supports or provides at least one of neurotransmission support, axon regeneration support, BACE1 metabolism/inhibition, tau-protein metabolism/inhibition, mitochondrial function support, and antioxidant protection.

Provided below are non-limiting benefits afforded by some of the active ingredients that are present in some embodiments of the compositions of the present disclosure.

All B-vitamins are water-soluble vitamins that are essential in healthy cell metabolism throughout the body and especially the brain. In some embodiments, Vitamin B3 (niacin) in the composition facilitates energy transfer reactions throughout the human body. In some embodiments, niacin acts as coenzyme in nucleic acid synthesis, promotes mitochondrial health and supports regeneration of axons of nerve cells. In some embodiments, niacin supports cardiovascular function and promotes the conversion of fats, proteins, carbohydrates, and starches into usable energy for the brain and body. In some embodiments, the brain can utilize this usable energy to maintain healthy functions like neurotransmitter production. In some embodiments, niacin also supports a healthy central nervous system.

In some embodiments, the composition comprises Vitamin B6 which is involved in amino acid metabolism and production as well as the breakdown of amino acids during fasting and endurance exercise. Vitamin B6 is also involved in niacin formation and glycogen breakdown for energy. Vitamin B6 is transported in red blood cells or bound to albumin. Vitamin B6 is fundamentally important in amino acid and glycogen metabolism, and has an important role in efficient energy metabolism. In some embodiments, Vitamin B6 promotes neurotransmission support, tau protein metabolism, and BACE1 metabolism. In some embodiments, Vitamin B6 also helps the body make several neurotransmitters, chemical messengers that carry signals from cell to cell. In some embodiments, Vitamin B6 aids in the production of the serotonin, norepinephrine and y-aminobutyrate (GABA), which may influence mood, emotions and appetite. In some embodiments, Vitamin B6 may help the body make melatonin, which helps regulate the body clock and sleep patterns.

In some embodiments, the composition comprises Vitamin B12 which is directly involved in the metabolism of folate. Vitamin B12 is also used in the breakdown of certain amino acid and fatty acids for ATP production, and assists in gluconeogenesis. The presence of Vitamin B12 in some compositions may also contribute to proper nerve function and in maintaining the special insulating myelin wrapping around nerve cells, important for neuromuscular communication. In some embodiments, Vitamin B12 assists in maintaining proper nerve function and in the energy production in every cell of the body. In some embodiments, this leads to improved neurotransmission and beneficial tau protein metabolism. Vitamin B12 may also aid in formation of red blood cells which deliver oxygen to all parts of the body and the brain. Thus, in some embodiments, Vitamin B12 in the formulation can contribute to nervous system health, cardiovascular wellness, physical performance, and mental acuity.

In some embodiments, the composition comprises Vitamin D. The pro-hormone Vitamin D, also known as cholecalciferol, is converted in the body to the active form calcitriol. Calcitriol regulates $Ca^{2+}$ transport throughout the body. Proper $Ca^{2+}$ concentrations are essential for proper neurotransmission in the synaptic gaps. In some embodiments, Vitamin D in the composition can promote mitochondrial health, neurotransmission support, and axon regeneration. In some embodiments, Vitamin D can promote cell health and growth in the brain and body. In some embodiments, Vitamin D can promote healthy bones, strong immune system functions and mental and emotional wellness.

In some embodiments, the composition comprises Acetyl L-Carnitine (ALCAR) which is the superior bioavailable form of the amino acid L-Carnitine and can cross the blood-brain-barrier. Acetyl L-Carnitine is involved in many metabolic functions in the human body including the transport of fatty acids into the cell for energy production. ALCAR is an antioxidant and its presence in the composition can protect brain cells by supporting neurotransmission, mitochondrial health and through its antioxidant capabilities. In some embodiments, Acetyl L-Carnitine helps maintain healthy neurological functions by delivering antioxidant protection throughout the entire nervous system. In some embodiments, Acetyl L-Carnitine in the composition supports cognitive health and optimal brain function, in turn enhancing alertness, concentration, and memory.

In some embodiments, the composition comprises Choline bitartrate which is the water-soluble form of choline and is an essential component of phosphatidylcholine and sphingomyelin. The Choline bitrate in the composition may promote the structural integrity of cell membranes. Choline is also a precursor to acetylcholine, a stimulatory neurotransmitter essential for normal synaptic transmission and brain health. In some embodiments, Choline and Inositol in the composition work closely together to make natural chemical messengers that help maintain brain and central nervous system function by supporting neurotransmission, mitochondrial health, and BACE1 metabolism. In some embodiments, a combination of Choline and Inositol may benefit attention, focus, recall and other higher brain functions.

In some embodiments, the composition comprises Inositol. Along with its metabolites, Inositol is involved in cell signaling and act as secondary messenger in a number of biological processes such as cell membrane potential protection, gene expression, and fat metabolism. Inositol is an essential component for the formation of cell membranes. In some embodiments, Inositol in the composition supports brain and nervous system health by its role in modulating serotonin activity. In some embodiments, Inositol has similar benefits to Choline bitartrate in regards to neurotransmission and mitochondrial health support, and BACE1 metabolism. In some embodiments, Inositol and Choline can work closely together to make natural chemical messengers that help maintain brain and central nervous system function. In some embodiments, a combination of Choline and Inositol may benefit attention, focus, recall and other higher brain functions.

In some embodiments, the composition comprises N-Acetyl L-Tyrosine which is the water soluble form of the amino acid tyrosine. L-Tyrosine is a key component in the production and transmission of neurotransmitters and in the composition can contribute to mental well-being. In some embodiments, N-Acetyl L-Tyrosine can support brain function and promotes neurotransmission support and antioxidant protection, for example by improving the synthesis of the neurotransmitters norepinephrine and dopamine. In some embodiments N-Acetyl L-Tyrosine in the composition contributes to mental health and alertness.

In some embodiments, the composition comprises L-Theanine which is an amino acid found in green tea and can easily cross the blood-brain barrier. L-Theanine has structural similarities with another amino acid, Glutamine, and also acts as a neurotransmitter. In some embodiments L-Theanine aids in reducing stress and promotes relaxation without causing drowsiness and counterbalances the negative effects of caffeine. In some embodiments L-Theanine promotes calm, balanced mental health and emotional well-being. In some embodiments L-Theanine helps manage daily tension while supporting sleep quality and mental acuity. In some embodiments L-Theanine acts as an antioxidant and aids the body's and brain's defenses against free radicals. In some embodiments L-Theanine acts as an antioxidant and aids the body's defenses against free radicals. In some embodiments L-Theanine acts as an antioxidant and aids the brain's defenses against free radicals. In some embodiments L-Theanine supports mitochondrial function.

In some embodiments, the composition comprises DMAE (dimethylaminoethyl) bitartrate, which is related in its chemical composition to choline and is incorporated into phospholipids of nerve membranes, where it acts on fluidity and permeability. In some embodiments, DMAE can promote neurotransmission and BACE1 metabolism. In some embodiments, DMAE may potentiate mental health and healthy cognitive function. In some embodiments, DMAE can function as a biochemical precursor to choline and acetylcholine, which can in turn influence cognitive function such as alertness, attention, memory and focus.

In some embodiments, the composition comprises PQQ (pyrroloquinoline quinone), which is a natural compound found in an array of healthy foods. In some embodiments, PQQ in the composition can act as an essential co-factor in cell signaling pathways involved in cellular energy metabolism. In some embodiments, PQQ can act as a strong antioxidant with neuroprotective effect. In some embodiments, PQQ can protect brain cells against oxidative damage and provide cognitive support as well as promote and maintain healthy mental function such as recall, memory and cognition. In some embodiments, PQQ can support nerve growth factor, and the growth and maintenance of healthy neurons and branching nerve cells. In some embodiments, as an antioxidant, PQQ can protect mitochondria against oxidative stress. In some embodiments, PQQ can promote the generation of new mitochondria inside aging cells potentially making the cells more energetic and act younger.

In some embodiments, the composition comprises caffeine. In some embodiments the caffeine may come from Green Tea extract. A trimethyl xanthine alkaloid, caffeine readily crosses the blood-brain-barrier and acts as a Central Nervous System stimulant. Thus, in some embodiments, caffeine in the composition induces mental alertness, focus, mental acuity and concentration. In some embodiments, caffeine can inhibit the negative effects adenosine has on neurotransmission, arousal, and pain perception. In some embodiments, caffeine can influence ATP and cAMP production. In some embodiments, a moderate dose of caffeine acts as an ergogenic aid. In some embodiments, caffeine can act as an antioxidant and supports neurotransmission.

In some embodiments, the composition comprises Vitamin E, also known as tocopherol, which is the fat-soluble equivalent to vitamin C. In some embodiments, Vitamin E in the composition can act as a strong antioxidant and protects cell membranes by neutralizing free radicals in the body and can promote cardiovascular health. In some embodiments, Vitamin E can prevent oxidation of cell membranes and protects them from oxidative damage. In some embodiments, Vitamin E can aid in maintaining the structure and function of the human nervous system.

In some embodiments, the composition comprises at least 4 of the following active ingredients: Acetyl L-Carnitine, Inositol, N-Acetyl L-Tyrosine, L-Theanine, pyrroloquinoline quinone (PQQ), Dimethylaminoethyl (DMAE) bitartrate, Vitamin E, Vitamin D, Niacin, Vitamin B6, Vitamin B12, and Green Tea extract. In some embodiments, the composition comprises at least 4, 5, 6, 7, 8, 9, 10, 11, 12 or all 13 of the active ingredients. In some embodiments, the composition may comprise additional active or inactive ingredients.

In some embodiments, the composition comprises at least 4 active ingredients that are synergistic in their effects. In some embodiments, the composition comprises at least 4, 5, 6, 7, 8, 9, 10, 11, 12 or 13 synergistic active ingredients. For example, the active ingredients may be synergistic with respect to their positive effects on vascular health and/or neuronal health.

In some embodiments, the effects of 4 or more of the active ingredients are additive. In some embodiments, the effects of at least 4, 5, 6, 7, 8, 9, 10, 11, 12 or 13 of the active ingredients are additive. For example the effects may be additive with respect to having a positive effect on vascular health and/or neuronal health.

In some embodiments, the effects of the at least 4-13 active ingredients are additive and synergistic.

In some embodiments, at least one of the active ingredients potentiates the positive effect on brain health of at least one other active ingredient. For example, at least one active ingredient may potentiate the positive effect of at least one other ingredient on neuronal health and/or vascular health.

In some embodiments, a liquid drink comprises Acetyl-L-Carnitine, Choline bitartrate, Inositol, N-Acetyl L-Tyrosine, L-Theanine, and PQQ. In some embodiments the liquid drink additionally comprises DMAE bitartrate.

In some embodiments, a liquid drink comprises Vitamin E, Vitamin D, Niacin, Vitamin B6, Vitamin B12, Acetyl-L-Carnitine, Choline bitartrate, Inositol, N-Acetyl L-Tyrosine, L-Theanine, DMAE bitartrate, PQQ and Green Tea extract.

In some embodiments niacin is present in the form of at least one of niacin, nicotinamide, and inositol hexanicotinate.

In some embodiments Vitamin E is present in the form of at least one of Vitamin E Acetate or mixed Tocopherols.

In some embodiment Vitamin D is present in the form of at least one of Vitamin D3 or Vitamin D2.

In some embodiments, the composition comprises the following active ingredients in the indicated amounts in one dose or serving of the composition, for example in a daily dose: 0.0001-2 g of Acetyl-L-carnitine; 0.0001-1 g of Choline bitartrate; 0.0001-1 g of Inositol; 0.0001-1 g of N-Acetyl L-tyrosine; 0.0001-800 mg of L-Theanine; and 0.0001-30 mg of PQQ.

In some embodiments, the composition comprises the following active ingredients in the indicated amounts in one dose or serving of the composition, for example in a daily dose:
  Vitamins D (0.0001-5,000 IU);
  Niacin (0.0001-200 mg);
  Vitamin B6 (0.0001-30 mg);
  Vitamin B12 (0.0001-3 mg);
  Acetyl-L-Carnitine (0.0001-2 g);
  Choline bitartrate (0.0001-1 g);
  Inositol (0.0001-1 g);
  N-Acetyl L-Tyrosine (0.0001-1 g);
  L-Theanine (0.0001-800 mg);
  DMAE bitartrate (0.0001-250 mg);
  PQQ (0.0001-30 mg);
  Green tea extract (0.0001-300 mg); and
  Vitamin E (0.0001-400 IU).

In some embodiments, the composition comprises about 0.0001-about 5,000 IU of Vitamins D per daily dose or serving.

In some embodiments, the composition comprises about 0.0001-about 200 mg of Niacin per daily dose or serving.

In some embodiments, the composition comprises about 0.0001-about 30 mg of Vitamin B6 per daily dose or serving.

In some embodiments, the composition comprises about 0.0001-about 3 mg of Vitamin B12 per daily dose or serving.

In some embodiments, the composition comprises about 0.0001-about 2 g of Acetyl-L-Carnitine per daily dose or serving.

In some embodiments, the composition comprises about 0.0001-about 1 g of Choline bitartrate per daily dose or serving.

In some embodiments, the composition comprises about 0.0001-about 1 g of Inositol per daily dose or serving.

In some embodiments, the composition comprises about 0.0001-about 1 g of N-Acetyl L-Tyrosine per daily dose or serving.

In some embodiments, the composition comprises about 0.0001-about 800 mg of L-Theanine per daily dose or serving.

In some embodiments, the composition comprises about 0.0001-about 250 mg of DMAE bitartrate per daily dose or serving.

In some embodiments, the composition comprises about 0.0001-about 30 mg of PQQ per daily dose or serving.

In some embodiments, the composition comprises about 0.0001-about 300 mg of Green Tea extract per daily dose or serving.

In some embodiments, the composition comprises about 0.0001-about 400 IU of Vitamin E per daily dose or serving.

As mentioned above, in some embodiments, the composition is an oral supplement. In some embodiments, the composition is an edible solid or an edible semi-solid. In a preferred embodiment, the composition is a potable liquid. In some embodiments, the composition is a powder or pellet that can be reconstituted in a potable liquid (e.g., water). In some embodiments, the composition is a tablet or a capsule that can be taken without reconstitution.

In some embodiments the composition is formulated as a single serving to be taken once per day by a subject. Thus, in some embodiments a daily dose of active ingredients is provided in a single serving. In some embodiments one daily dose may be divided among two or more servings to be taken in a day, for example among two or more servings of a liquid beverage or two or more tablets. A daily dose of the composition is preferably taken by or administered to a subject in a 24 hour period. In some embodiments, a daily dose of the composition is taken every day for 1 week to 12 months. In some embodiments, the composition is taken for 1, 2, 3 or 4 weeks. In some embodiments, the composition is taken for 2, 3, 4, 5, 6, 7, 8, 9, 10, 11 or 12 months.

In some embodiments, the composition is taken in the morning on an empty stomach. In some embodiments, the composition is taken at any time mental focus and clarity is needed. In some embodiments, the composition is taken daily to promote brain health. In some embodiments, the composition is taken to promote restful sleep. In some embodiments, the composition is taken to promote a feeling of overall well-being.

As mentioned above, in some embodiments a daily dose of the composition can be provided in one or more daily servings. In some embodiments a daily dose is provided in a single serving. In some embodiments a daily dose may be provided in two or more servings (up to 5 servings in 24 hours). While the size of each serving may vary, the quantity of active ingredients to be consumed will be equal to one serving. In the case of a single serving, where one single serving is intended to be taken per day, the single serving will comprise a complete daily dose. In the case of multiple servings, the quantity of active ingredients will be such that the total amount of active ingredients in the servings to be taken in a single day is equivalent to a daily dose.

In some embodiments, the composition is a liquid drink comprising a single serving of about 4.5 fl. oz. However, the skilled artisan will appreciate that while the size of the serving itself may vary depending on the quantity of the inactive ingredients, such as water, the amount of the active ingredients in each single serving will be within the ranges provided herein. For example, while the single serving size may be ½ fl. oz, 1 fl. oz, 2 fl. oz., 4 fl. oz., 6 fl. oz., 10 fl. oz., 12 fl. oz., 16 fl. oz. or anything smaller or larger, the daily dose of active ingredients will be the same in each serving. In some embodiments a single serving is about 2 fl. oz. to about 54 fl. oz. In some embodiments, the composition is a liquid concentrate comprising of multiple servings to be diluted into a liquid beverage to obtain 1 serving sizes.

In some embodiments, the composition comprises additional components that improve absorption of one or more of the active ingredients.

In some embodiments, general health improvements observable after taking the composition may include improvements to vascular health, improvements to neuronal health and/or improvements to brain health. In some embodiments, the improvements to brain health may include, but are not limited to, high levels of concentration, optimal cognitive function, effective decision making, keen comprehension, effortless recall, mental clarity, quick reflexes, restful sleep, increased motivation, coordinated motor function, efficient problem solving, mental acuity, optimal energy levels, overall well-being, ability to focus, mood stability, memory support, alertness, improved neurotransmission, and nerve cell integrity.

In some embodiments, the composition may be seen to provide benefits to subjects suffering from Post Traumatic Stress Disorder (PTSD), Attention Deficit Disorder (ADD), Attention Deficit Hyperactivity Disorder (ADHD), anxiety, migraine, dementia, tinnitus, and in hangovers.

In some embodiments, a health improvement kit is provided which comprises compositions according to some embodiments disclosed herein and a dietary plan comprising instructions to use the compositions in the kit to improve human health, particularly brain health. In some embodiments, the dietary plan can comprise taking at least one (1) serving of the composition per day, for example in the form of a liquid beverage of about 4.5 fl. oz. In some embodiments, at least one serving can be taken in the morning on an empty stomach. In some embodiments, at least one serving can be taken at any time mental focus and clarity is needed. In some embodiments, at least two servings can be taken at any time mental focus and clarity is needed. In some embodiments, a maximum of five servings in a 24 hour period can be taken at any time mental focus, clarity and mental well-being is needed. In some embodiments, at least 1, 2, 3, 4, or 5 servings can be taken at any time that any one or more of: improvements to vascular health, improvements to neuronal health, and/or improvements to brain health (including, but not limited to the following: high levels of concentration, optimal function, effective decision making, keen comprehension, effortless recall, mental clarity, quick reflexes, restful sleep, increased motivation, coordinated motor function, efficient problem solving, mental acuity, optimal energy levels, overall well-being, ability to focus, mood stability, memory support, alertness, improved neurotransmission, and nerve cell integrity) is needed or desired.

In some embodiments, the kit comprises a composition that is an edible solid or an edible semi-solid. In a preferred embodiment, the composition in the kit is a potable liquid. In some embodiments, the composition in the kit is a powder or pellet that can be reconstituted in a potable liquid (e.g., water). In some embodiments, the composition in the kit is a tablet or a capsule that can be taken without reconstitution.

TABLE 1 provides a non-limiting example of an embodiment of a composition formulated as a liquid drink comprising active and inactive ingredients. The amount per serving (for example a daily dose in a 4.5 fl. oz liquid drink.) for the components are listed.

TABLE 1

| | Amount Per Serving |
|---|---|
| Vitamin D3 (as cholecalciferol) | 400 IU |
| Vitamin E (as mixed tocopherols) | 30 IU |
| Niacin (as niacinamide) | 100 mg |
| Vitamin B6 (as pyridoxine HCl) | 15 mg |
| Vitamin B12 (as cyanocobalamin) | 500 µg |
| Acetyl-L-Carnitine | 500 mg |
| Choline bitartrate | 300 mg |
| Inositol | 250 mg |
| N-Acetyl L-Tyrosine | 250 mg |
| L-Theanine | 200 mg |
| DMAE bitartrate | 75 mg |
| Green Tea Extract | 70 mg |
| PQQ (Pyrroloquinoline Quinone) | 5 mg |

Other non-limiting ingredients in the composition of TABLE 1 can include Water, Cane sugar, Natural flavors, Citric acid, Stevia extract and Talin.

What is claimed is:

1. A liquid drink comprising Acetyl-L Carnitine, Choline bitartrate, Inositol, N-Acetyl L-Tyrosine, L-Theanine, pyrroloquinoline quinone (PQQ), Dimethylaminoethanol (DMAE) bitartrate, Vitamin E, Vitamin D, Niacin, Vitamin B6, Vitamin B12, and Green tea extract.

2. The liquid drink of claim 1, additionally comprising one or more of alpha-GPC (alpha-glycerylphosphorylcholine), Citicholine, Phosphatidylserine, Astaxanthin, Flaxseed, MCT (Medium Chain Triglycerides), Whole Coffee Fruit extract, *Ginko biloba*, Vinpocetine, *Panax ginseng*, Ashwaghanda, *Bacopa monnieri*, Grape seed extract, omega-3 fatty acids, omega-6 fatty acids, omega-9 fatty acids, Huperzine A, alpha-Lipoic acid, Magnesium and Zinc.

3. The liquid drink of claim 1, additionally comprising one or more natural flavors and/or natural sweeteners.

4. The liquid drink of claim 3, wherein the liquid drink comprises one or more of sugar, fructose, honey, erythritol, xylitol, stevia, talin, monk fruit, agave, citrus and protein extracts.

5. The liquid drink of claim 1, additionally comprising one or more of propylene glycol, xanthan gum, guar gum, acacia gum; fillers; rice flour, methylcellulose, magnesium stearate.

6. The liquid drink of claim 1, additionally comprising one or more flavoring agents.

7. The liquid drink of claim 1, comprising 0.0001-2 g of Acetyl-L-carnitine; 0.0001-1 g of Choline bitartrate; 0.0001-1 g of Inositol; 0.0001-1 g of N-Acetyl L-tyrosine; 0.0001-800 mg of L-Theanine; and 0.0001-30 mg of PQQ.

8. The liquid drink of claim 1, comprising 0.0001-5,000 IU of Vitamin D; 0.0001-200 mg of Niacin; 0.0001-30 mg of Vitamin B6; 0.0001-3 mg of Vitamin B12; 0.0001-2 g of Acetyl-L-carnitine; 0.0001-1 g of Choline bitartrate; 0.0001-1 g of Inositol; 0.0001-1 g of N-Acetyl L-tyrosine; 0.0001-800 mg of L-Theanine; 0.0001-250 mg DMAE bitartrate; 0.0001-30 mg of PQQ; 0.0001-300 mg of Green Tea extract; and 0.0001-400 IU of Vitamin E.

9. The liquid drink of claim 1, wherein a single serving of the liquid drink is about 2 fl. oz to about 5 fl. oz.

10. A method of improving brain health in a human subject, the method comprising administering to the human subject a composition comprising Acetyl L-Carnitine, Choline bitartrate, Inositol, N-Acetyl L-Tyrosine, L-Theanine, pyrroloquinoline quinone (PQQ), Dimethylaminoethanol (DMAE) bitartrate, Vitamin E, Vitamin D, Niacin, Vitamin B6, Vitamin B12, and Green tea extract.

11. The method of claim 10, wherein the composition comprises 0.0001-2 g of Acetyl-L-carnitine; 0.0001-1 g of Choline bitartrate; 0.0001-1 g of Inositol; 0.0001-1 g of N-Acetyl L-tyrosine; 0.0001-800 mg of L-Theanine; and 0.0001-30 mg of PQQ.

12. The method of claim 10, wherein the composition comprises 0.0001-5,000 IU of Vitamin D; 0.0001-200 mg of Niacin; 0.0001-30 mg of Vitamin B6; 0.0001-3 mg of Vitamin B12; 0.0001-2 g of Acetyl-L-Carnitine; 0.0001-1 g of Choline bitartrate; 0.0001-1 g of Inositol; 0.0001-1 g of N-Acetyl L-Tyrosine; 0.0001-800 mg of L-Theanine; 0.0001-250 mg DMAE bitartrate; 0.0001-30 mg of PQQ; 0.0001-300 mg of Green tea extract; and 0.0001-400 IU of Vitamin E.

13. The method of claim 10, wherein the composition additionally comprises one or more of alpha-GPC (alpha-glycerylphosphorylcholine), Citicholine, Phosphatidylserine, Astaxanthin, Flaxseed, MCT (Medium Chain Triglycerides), Whole Coffee Fruit extract, *Ginko biloba*, Vinpocetine, *Panax ginseng*, Ashwaghanda, *Bacopa monnieri*, Grape seed extract, omega-3 fatty acids, omega-6 fatty acids, omega-9 fatty acids, Huperzine A, alpha-Lipoic acid, Magnesium and Zinc.

14. The method of claim 10, wherein the composition comprises one or more of sugar, fructose, honey, erythritol, xylitol, stevia, talin, monk fruit, agave, citrus and protein extracts.

15. The method of claim 10, wherein the composition additionally comprises one or more of propylene glycol, xanthan gum, guar gum, acacia gum; fillers; rice flour, methylcellulose, and magnesium stearate.

16. The method of claim 10, wherein the composition is administered in the form of a liquid drink.

17. The method of claim 16, wherein a single serving of the liquid drink is about 4.5 fl. oz.

\* \* \* \* \*

UNITED STATES PATENT AND TRADEMARK OFFICE
CERTIFICATE OF CORRECTION

PATENT NO. : 10,449,148 B2
APPLICATION NO. : 15/287346
DATED : October 22, 2019
INVENTOR(S) : Patricia Gutierrez et al.

Page 1 of 2

It is certified that error appears in the above-identified patent and that said Letters Patent is hereby corrected as shown below:

On the Title Page

Column 1, Item (56), Line 8, under Other Publications, delete "4-methylenedioximehtamphetamine" and insert --4-methylenedioxymethamphetamine--.

On Page 2, Column 2, Item (56), Line 7, under Other Publications, delete "Inisitol" and insert --Inositol--.

On Page 2, Column 1, Item (56), Line 9, under Other Publications, delete "Tyrpsine," and insert --Tyrosine,--.

On Page 3, Column 2, Item (56), Line 49, under Other Publications, delete "Extention" and insert --Extension--.

On Page 4, Column 2, Item (56), Line 38, under Other Publications, delete "white-majer" and insert --white-matter--.

On Page 4, Column 1, Item (56), Line 9, under Other Publications, delete "Extention" and insert --Extension--.

On Page 4, Column 1, Item (56), Line 13, under Other Publications, delete "Psychopharmocology," and insert --Psychopharmacology,--.

In the Specification

In Column 1, Line 52, delete "Citicholine," and insert --Citicoline,--.

In Column 1, Line 54, delete "*Ginko*" and insert --*Ginkgo*--.

In Column 1, Line 55, delete "Ashwaghanda," and insert --Ashwagandha,--.

Signed and Sealed this
Seventh Day of April, 2020

Andrei Iancu
*Director of the United States Patent and Trademark Office*

CERTIFICATE OF CORRECTION (continued)
U.S. Pat. No. 10,449,148 B2

In Column 2, Line 23, delete "Citicholine," and insert --Citicoline,--.

In Column 2, Line 25, delete "*Ginko*" and insert --*Ginkgo*--.

In Column 2, Line 26, delete "Ashwaghanda," and insert --Ashwagandha,--.

In Column 3, Line 28, delete "Citicholine," and insert --Citicoline,--.

In Column 3, Line 30, delete "*Ginko*" and insert --*Ginkgo*--.

In Column 3, Line 31, delete "Ashwaghanda," and insert --Ashwagandha,--.

In the Claims

In Column 10, Line 63, Claim 1, delete "Acetyl-L Carnitine," and insert --Acetyl-L-Carnitine,--.

In Column 11, Line 3, Claim 2, delete "Citicholine," and insert --Citicoline,--.

In Column 11, Line 5, Claim 2, delete "*Ginko*" and insert --*Ginkgo*--.

In Column 11, Line 6, Claim 2, delete "Ashwaghanda," and insert --Ashwagandha,--.

In Column 11, Line 18, Claim 5, delete "acacia gum; fillers;" and insert --acacia gum, fillers,--.

In Column 12, Line 20, Claim 13, delete "Citicholine," and insert --Citicoline,--.

In Column 12, Line 22, Claim 13, "*Ginko*" and insert --*Ginkgo*--.

In Column 12, Line 23, Claim 13, delete "Ashwaghanda," and insert --Ashwagandha,--.

In Column 12, Line 33, Claim 15, delete "acacia gum; fillers;" and insert --acacia gum, fillers,--.